(12) United States Patent
Dekkers et al.

(10) Patent No.: US 7,663,000 B2
(45) Date of Patent: Feb. 16, 2010

(54) QUINONEIMINES OF MALONIC ACID DIAMIDES

(75) Inventors: David Walterus Cornelius Dekkers, Veldhoven (NL); Lucien Adrianus Aarden, Broek in Waterland (NL); Janna Alberdina Ten Brinke, Utrecht (NL)

(73) Assignee: A-Viral ASA, Lysaker (NO)

( * ) Notice: Subject to any disclaimer, the term of this patent is extended or adjusted under 35 U.S.C. 154(b) by 380 days.

(21) Appl. No.: 10/565,506

(22) PCT Filed: Jul. 23, 2004

(86) PCT No.: PCT/GB2004/003189
§ 371 (c)(1),
(2), (4) Date: Oct. 2, 2006

(87) PCT Pub. No.: WO2005/011664
PCT Pub. Date: Feb. 10, 2005

(65) Prior Publication Data
US 2007/0112072 A1     May 17, 2007

(30) Foreign Application Priority Data
Jul. 23, 2003    (GB) ................. 0317268.1

(51) Int. Cl.
C07C 233/05    (2006.01)
A61K 31/16     (2006.01)
(52) U.S. Cl. ...................... 564/158; 514/616
(58) Field of Classification Search ............. 564/158; 514/616
See application file for complete search history.

(56) References Cited

FOREIGN PATENT DOCUMENTS

| DE | 25 31 836 A | 2/1976 |
|----|-------------|--------|
| EP | 1 411 046 A | 4/2004 |
| WO | 03/000660 A1 | 1/2003 |
| WO | 2004/055175 A | 7/2004 |

OTHER PUBLICATIONS

Vennerstrom et al, J. Med. Chem., 1987, vol. 30, 434-437.*
Farmatsevtichnii Zhurnal, vol. 1, 1998, pp. 78-81, XP009039952.
Ukrainets et al., "Ethyl esters of malonanilic acids. Synthesis and pyrolysis", Tetrahedron, Elsevier Science Publishers, Amsterdam, NL., vol. 50, No. 34, 1994, pp. 10331-10338, XP002130231.
Database Caplus 'Online! Chemical Abstracts Service, Columbus, Ohio, US; XP002305721 Accession No. 2003:626770 Database accession No. 140:228413 abstract & Klinichna Farmatsiya, vol. 7, No. 1, 2003, pp. 63-66.
Database Caplus 'Online! Chemical Abstracts Service, Columbus, Ohio, US: XP002305722 accession No. 1992:531129, Database accession No. 117:131129 abstract & Khimiya Geterotsiklicheskikh Soedinenii, vol. 11, 1999, pp. 1521-1527.
Database Caplus 'Online! Chemical Abstracts Service, Columbus, Ohio, US; XP002305723 accession No. 1970:31396, Database accession No. 72:31396 abstract & Journal of the Indian Chemical Society, vo. 66, No. 9, 1969, pp. 857-859.
Database Caplus 'Online! Chemical Abstracts Service, Columbus, Ohio, US; XP002305724 Accession No. 1957:62310, Database accession No. 51:62310 abstract & Helvetica Chimica Acta, vol. 40, 1957, pp. 395-401.

* cited by examiner

*Primary Examiner*—Shailendra Kumar
(74) *Attorney, Agent, or Firm*—Bacon & Thomas, PLLC (57) ABSTRACT

The present invention provides optionally substituted compounds of the formula I or salts thereof;

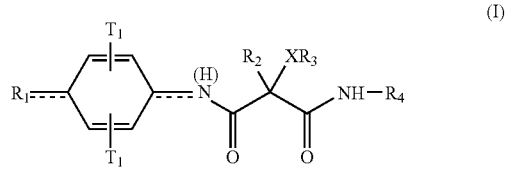

(I)

wherein $R_1$ is O or S when double bonded to the ring or is OH, SH, or a protected equivalent, when single bonded to the ring, $R_2$ is hydrogen or more preferably an $C_1$-$C_{10}$ organic group attached by a carbon atom, X is H, O, OO, S or SS $R_3$ is absent where X=H, is hydrogen or is a hydroxyl or thiol protecting group, $R_4$ is a hetero- or preferably homo-cyclic aryl group, optionally substituted with a further group $R_5$ and groups $T_1$ are each, independently, absent, hydrogen or an S—$R_6$ group, where any/each $R_6$ is independently an organic group of molecular weight up to around 500 amu. The invention further provides a method for the synthesis of such compounds and a method of treatment comprising administering such compounds to a mammalian subject.

12 Claims, 8 Drawing Sheets

QUINONEIMINES OF MALONIC ACID DIAMIDES

This application is a 371 of PCT/GB04/03189, filed Jul. 23, 2004.

The present invention relates to certain quinone compounds and the use thereof in therapy. More particularly, the present invention relates to such compounds and their use as anti-inflammatory, anti-viral and immunomodulatory agents.

The cyclic pyrazolidine dione compounds phenbutazone, oxyphenbutazone and 4-hydroxy oxyphenbutazone are known or suggested as having anti-inflammatory, antiviral and/or immunomodulatory properties.

Phenbutazone (PB)

Oxyphenbutazone (OPB)

4-Hydroxy OPB (4OH-OPB)

Many derivatives of these pyrazole based structures have been investigated, including derivatives (e.g. U.S. Pat. No. 3,968,219), and prodrugs (e.g. U.S. Pat. No. 4,117,232, U.S. Pat. No. 3,957,803, U.S. Pat. No. 4,169,147, U.S. Pat. No. 4,036,845 and U.S. Pat. No. 4,139,709). All related compounds showing biological activities have, however, retained the central, cyclic pyrazolidine core.

The present inventors have now, unexpectedly, established that a new class of related compounds exists in which the central pyrazoladinedione moiety is replaced with a linear, substituted, 5-atom chain of two nitrogens and three carbons.

In a first aspect, the present invention therefore provides an optionally substituted compound of the formula I (particularly a compound of formula Ia or Ib) or a salt thereof:

wherein $R_1$ is O or S when double bonded to the ring or is OH, SH, or a protected equivalent, when single bonded to the ring (suitable protective groups include those described herein for $R_3$), $R_2$ is hydrogen or more preferably an $C_1$-$C_{10}$ organic group attached by a carbon atom, e.g. an optionally substituted alkyl, alkenyl, alkynyl, alkaryl, aralkyl arylsupholnylalkyl or aralkenyl group, X is H, O, OO, S or SS, $R_3$ is absent (where X=H), is hydrogen or is a hydroxyl or thiol protecting group (e.g. a, preferably $C_2$-$C_7$ acyl, or alkaryl group, such as an acetyl or benzyl group), $R_4$ is a hetero- or preferably homo-cyclic aryl group, optionally substituted with a further group $R_5$ (e.g. with an alkyl, alkenyl, alkynyl, OH, O-alkyl, thio, thioalkyl, halo, or primary, secondary, tertiary or quaternary amino group) and groups $T_1$ are each, independently, absent (at the 1, or 4, positions relative to $R_1$), hydrogen (at any position but particularly the 2, or 3, position) or an S—$R_6$ group, where each $R_6$ is independently an organic group of molecular weight up to around 500 amu, such as a substituted or unsubstituted alkyl, alkenyl, alkynyl, alkaryl, aralkyl, alkyl ester, alkyl amide, alkyl acid, polyol, sugar, oligo(alkylamide), oligo(alkylester), or oligopeptide group. Where 1 or more S—$R_6$ groups are present, these may (independently) be ipso, ortho, meta or para to group $R_1$, but evidently only a maximum of 1 ipso group and a maximum of 1 para group may be present.

Preferred configurations for groups $T_1$ include those shown in formulae Ia and Ib. It is especially preferred that the compounds of the invention are of formula Ia wherein both $T_1$ groups are H or of formula Ib wherein both $T_1$ groups are independently S—$R_6$ groups.

It will be evident to a skilled worker that isomers of the compounds of formula I may exist. For example, in compounds such as those of formula I having a hydrogen as $T_1$ para to the $R_1$ group (and thus the nitrogen single bonded to the ring) but the $R_1$ group double-bonded to the ring (the other $T_1$ group being, for example at the meta or ortho position), isomerism to aromatise the ring to the corresponding Ar—SH or AR—OH compound (e.g. phenol) may occur. Evidently, such isomers will be in some degree of equilibrium with the compound of formula I and all such isomers will fall within the scope of the invention. An exactly corresponding isomerism may take place where the $R_1$ group is single-bonded and the nitrogen double-bonded to the ring. Similarly, where one $T_1$ is para to $R_1$, a stereo centre may be generated at the carbon para to $R_1$ and optical isomers (enantiomers and/or diastereomers where other asymmetric centres, such as the carbon attached to $R_2$, are present) of the compounds of formula I may be possible. These examples and all tautomeric and stereo isomers and mixtures thereof fall within the scope of the compounds of formula I. A small number of examples (wherein all groups $R_1$-$R_6$ and $T_1$ are as defined herein) of such compounds are shown below. Obviously these and their tautomers and stereoisomers fall within the scope of the present invention:

The present inventors have also established that compounds of the invention may be conveniently prepared by the ring-opening of certain well known starting materials.

In a further aspect, the present invention therefore provides a method for the synthesis of a compound by ring-opening of a starting material of formula II (II)

Wherein $T_1$, $R_1$, $R_2$, $R_3$, $R_4$ and X are as herein described, or protected derivatives or precursors thereof. Such starting materials are typically oxyphenbutazones or 4-hydroxy-oxyphenbutazones and are synthesised by methods described herein and by methods known in the art, such as from WO 01/00585 and the references cited therein. The disclosure contained in this document and in all references cited herein is hereby incorporated herein by reference.

Specifically, 4-hydroxyoxyphenbutazones may be synthesised from oxyphenbutazones by oxidation of corresponding compounds in which the $R_3X$ Position is occupied by hydrogen; from other 4-OH OPBs by reaction of corresponding compounds in which $R_3X$ is HX with hydroxy or thiol protecting groups to introduce non-hydrogen $R_3$ group, or by condensation of a hydrazine compound with an optionally protected 2-hydroxy-propane dioic acid halide, ester or similar compound, e.g.

wherein $T_1$, $R_1$-$R_4$ and X are as defined above for the starting materials and the groups L are leaving groups such as halides etc. Where X is H, oxyphenbutazones will result, which may be converted to 4-OH OPBs as described above. Where X is O, 4-OH OPBs will be formed directly.

As will be readily appreciated, the hydrazines may be prepared by hydrogenation of the corresponding diarylazo compounds (since $R_4$ is aryl), which in turn can be synthesised from simple aromatic nitro compounds in the presence of $LiAlH_4$ The group $T_1$ may be the same as $T_1$ in the linear compound of the invention, such as hydrogen or a substituted thiol, or may be initially hydrogen and be substituted with a thiol, such as glutathione in a later step, following cyclisation and optionally also following ring-opening. In a preferred method, groups $T_1$ are absent or are hydrogen at the ring forming stage and any S—$R_6$ groups present in the final compound are introduced after cyclisation and optionally after ring-opeining.

In a further aspect, the present invention provides a compound obtained or obtainable by ring opening of a starting material of formula II as defined herein. Preferably, such compounds are obtainable by ring opening of a preferred starting material as defined herein.

The present inventors have further, unexpectedly, established that compounds of the present invention have considerable utility as modulators of inflammatory and immune reactions within the body and in the treatment of certain conditions, particularly viral, inflammatory, neoplastic, allergic and autoimmune conditions. The compounds of the present invention may also provide a "tonic" effect in subjects suffering from fatigue, lethargy or the effects of aging, whether or not any direct, identifiable, cause of these symptoms is evident.

In a further aspect, the present invention therefore provides a method of treatment of a mammalian (preferably human) subject comprising administering a compound of formula I or a salt thereof as defined herein. In a preferred embodiment, the present invention provides a method of treatment of a viral, inflammatory, neoplastic, allergic or autoimmune condition (particularly disease) or of the symptoms of fatigue, lethargy or old age by administration of at least one compound of the present invention. Preferably, the compound will be a preferred compound, as described herein.

In a further aspect the present invention provides a compound of formula I or a salt thereof as defined herein for use in therapy. Preferably, the compound will be a preferred compound as described herein.

In a still further aspect, the present invention provides the use of a compound of formula I or a salt thereof as defined herein in the manufacture of a medicament. Preferably, this will be a medicament for the treatment of a viral, inflammatory, neoplastic, allergic or autoimmune condition (particularly disease) or of the symptoms of fatigue, lethargy or old age. Preferably, the compound will be a preferred compound as described herein.

Compounds of the present invention may be usefully administered in the form of a pharmaceutical composition, particularly for the treatment of disease. Alternatively, the compounds of the present invention may be taken in the form of an "functional food", a supplement or as a food or beverage fortification, particularly where a "tonic" effect in the reduction of the symptoms of fatigue, lethargy or old age or a general boost to the immune system is desirable.

In a yet still further aspect, the present invention therefore provides a pharmaceutical composition comprising a compound of the invention (i.e. of formula I) or a salt thereof as defined herein and at least one pharmaceutically acceptable excipient, carrier or diluent. The invention also provides a functional or fortified food comprising a compound of formula I or a salt thereof formulated in an edible food or potable beverage.

Preferred compounds of the invention are of formula III, and salts thereof. In particular, compounds of formulae IIa and IIIb (and salts thereof) are highly preferred;

wherein $T_1$, $R_2$ and $R_3$ are as described above and $R_5$ is hydrogen or an alkyl, alkenyl or alkynyl group (such as those listed infra for $R_2$), OH, O-alkyl, O-acyl, SH, S-alkyl, S-acyl, halo, or primary, secondary, tertiary or quaternary amino group. Preferred $R_5$ groups are hydrogen, OH and O-acyl (e.g O-acetyl). Most preferred are hydrogen, OH and O-acetyl.

In the compounds and starting materials of the invention, $R_2$ is preferably a $C_1$ to $C_6$ alkyl, alkenyl, or alkynyl group, (e.g. a methyl, ethyl, ethylenyl, acetylenyl, n-propyl, i-propyl, prop-1-enyl, prop-2-enyl, n-butyl, i-butyl, s-butyl, t-butyl, but-1-enyl, but-2-enyl, but-3-enyl, 1-methyl-prop-l-enyl, 1-methyl-prop-2-enyl, 2-methyl-prop-l-enyl, 2-methyl-prop-2-enyl, n-pentyl, i-pentyl etc.) or an arylsulphonylalkyl group such as phenylsuphonylmethyl. More preferably $R_2$ is $C_2$ to $C_6$alkyl, particularly n-butyl, i-butyl, s-butyl or t-butyl. The most preferred $R_2$ group is n-butyl.

$R_3$ in the compounds and starting materials described herein is preferably hydrogen or a metabolically labile protecting group which yields a physiologically tolerable byproduct. Suitable protecting groups are acyl groups, particularly acetyl, propanoyl, methylpropanoyl or n-butanoyl. Many additional OH and SH protecting groups are however known (see e.g. Greene, "protective groups in organic synthesis", Wiley Interscience, NY, 1981) and these may be of value as products, or particularly as intermediates. Most preferred $R_3$ groups are hydrogen and acetyl.

In the compounds and starting materials of the present invention, $T_1$ is preferably H or a thiol group, especially one substituted with an $R_6$ group (i.e. —S—$R_6$), where $R_6$ is a targeting moiety or a small (esp MW<500) organic group having at least two functional groups selected from esters, amides, carboxylic acids, hydroxyl groups and amines. It is preferred that either both $T_1$ groups are H or both are thiols (although the $R_6$ groups may be the same or different). Preferably, $R_6$ is an oligo ester or oligo peptide (i.e. a compound containing one or more ester or amide bonds) with at least one free acid and/or amine group. Examples of such groups include specific binding peptides such as antibody fragments. More preferably, each $T_1$ is independently hydrogen, a thio amino acid (e.g. cysteine) or a 2-5 residue oligo peptide (bonded via a sulfur atom). Most preferably, $T_1$ is independently hydrogen or glutathione. That is to say, both $T_1$ groups may be hydrogen, both may be glutathione, or one may be glutathione and the other hydrogen. The $T_1$ groups may be present in any configuration around the attached ring but two preferred structures are shown as formulae IIIa and IIIb. Of these, it is most preferred that in IIIa both $T_1$ groups are H and in IIIb, both $T_1$ groups are independently S—$R_6$.

The most preferred compound of the present invention is of formula IV or a salt thereof. Particularly preferred examples are shown as IVa and IVb;

-continued

(IVa)

(IVb)

wherein $R_5$ is hydrogen or OH and each $T_1$ is, independently, H or a glutathione moiety attached via the sulphur atom thereof.

Preferred methods for the synthesis of compounds of formula I comprise ring opening of starting materials of formula (V);

(V)

wherein the groups $T_1$, $R_2$, $R_3$ and $R_5$ are as described above and are preferably the preferred groups described above. In the most preferred starting material, $R_1$ is OH, $R_2$ is $C_4H_9$ (preferably n-butyl), $R_3$ is H and $R_5$ is H or OH.

In the starting materials, it is preferred that groups $T_1$ be absent or be hydrogen. $T_1$ groups of formula —S—$R_6$ may then be introduced during or after the ring opening of the compounds of formula II and especially formula V.

The ring opening of the starting materials may be carried out by re-arrangement in aqueous solution, particularly in neutral or slightly basic aqueous solution at temperatures between 0° C. and 100° C., preferably between 20° C. and 60° C. for a period of 30 seconds to 4 hours, preferably 4 minutes to 1 hour, most preferably 10 to 45 minutes. In some cases the compound of formula I resulting from the ring-opening reaction will be labile to hydrolysis but will generally have a longer lifetime than its rate of formation from the starting material. In such cases, the reaction time will preferably be shorter than the half-life of the product under the conditions of the reaction.

The progress of the ring-opening reaction will be conveniently followed by techniques well known in the field of organic chemistry such as Nuclear Magnetic Resonance (NMR) spectroscopy, Infra-Red (IR) spectroscopy and/or mass spectrometry. In particular, the appearance of the quinone moiety provides characteristic peaks in the NMR and infrared spectra. This allows the formation and stability of the product under the reaction conditions to be easily monitored and conditions optimised.

Medical conditions suitable for treatment, prevention or control by administration of the compounds, formulations, compositions or medicaments of the present invention include viral, autoimmune, neoplastic, inflammatory and allergic conditions including those which are secondary to other conditions and those having a viral, autoimmune, neoplastic, inflammatory or allergic component. Examples of immune, autoimmune, inflammatory and allergic conditions or conditions having a contribution from these mechanisms include Addison's disease, allergic conditions such as hay fever, food (e.g. nut, wheat or seafood) allergies or skin allergies, Alzheimer's disease, amyloidosis, (such as that resulting from conditions such as arthritis or tuberculosis), ankylosing spondylitis, asthma, antiplastic anemia, Behcet's disease, Bechterew's disease, Cogan's syndrome, Crohn's disease, dermatomyositis, diabetes mellitus, eczema, glandular disorders (such as diabetes, especially type II, and hypo- or hyper-thyroidism), glomerulonephritis, haemolytic anemia, Hepatitis Huntinton's disease, inflammatory bowel diseases such as irritable bowel syndrome, immune suppression (such as due to infection with HIV, compromised bone marrow function, treatment with cytotoxic chemotherapeutic agents etc.), liver diseases such as autoimmune hepatitis or primary biliary cirrhosis, lung diseases such as interstitial lung disease, lupus erythematosus, Morbus Reiter, neoplastic disease (such as benign or particularly malignant neoplasms e.g cancer (sarcoma or carcinoma), leukemia etc.), neurological disorders such as multiple sclerosis or myasthenia gravis, inflammatory or autoimmune ocular disorders such as scleritis or uveitis, post-operative ocular inflammation, or resulting from Behcet's disease, osteoarthritis, Parkinson's disease, pemphigus, polyglandular deficiency, polymyositis, pernicious anemia, psoriasis, rheumatoid arthritis and other rheumatic disorders (such as Besnier's rheumatism, rheumatic fever, lumbago, or Poncet's rheumatism), sarcoidosis, scleroderma, Sjögren's syndrome, testicular failure, thrombocytopenic purpura, tissue rejection and prevention thereof, ulcerative colitis and Wegner's granulomatosis. Examples of viruses and viral conditions which may be treated, prevented and controlled include viral infections of CD4 cells (e.g. HIV-1, HIV-2, HTLV-I, HTLV-II and herpes viruses), togaviridea, reoviradea, picornaviradea, hantaviridea, orthomyxoviridea, paramyxoviridea, mononegaviralis, viral hepatitis, haemorrhagic fever, flaviviridea, viral encephalitis, coronoviridea, calciviridea, adenoviridea, papoviridea, arboviridea, pox virus, rhabdoviridea, and arenaviridea. Examples of neoplastic diseases include solid tumours and neoplastic haematological disorders such as leukaemias.

The thiol substituted compounds of the present invention (wherin at least 1 $T_1$ group is S—$R_6$), may be formed by thiol derivatisation of the corresponding compounds wherein one or both $T_1$ groups is hydrogen. The derivatisation may be carried out in vitro (see examples infra) or may happen in vivo by reaction with naturally ocurring thiols such as glutathione. In one embodiment, the invention provides a method of forming the compounds of formula I in which at least one $T_1$ group is S—$R_6$ by administering to a subject a compound of formula I in which both $T_1$ groups are hydrogen. This method may also be used to convert the second $T_1$ group to S—$R_6$, where mono-substitution is already present (i.e. where one $T_1$ group is already S—$R_6$).

The thiol derivatised compounds of the present invention (i.e. where at least one $T_1$ group is not H) may additionally be advantageous because the positions containing thiol substituents are not availble for reaction with thiols in vivo. Excessive consumption of naturally ocurring thiols such as glutathione may damage or even kill cells and thus these derivatised compounds may show lower,toxicity and/or fewer side effects.

Where the compounds, compositions or medicaments of the invention are administered to combat primary or secondary diseases, these may be in combination with other active agents, either as a combined formulation or as separate formulations administered simultaneously or sequentially. In particular, where the compositions of the invention are administered to combat a secondary disease, this will typically be simultaneously with, or following, treatment for the primary condition. For example, the compositions of the present invention may be administered in combination with antiviral agents (such as nucleoside analogues) in order to combat the viral disease and provide improved quality of life for the subject.

Compounds of the present invention may be formulated as pharmaceuticals by methods well known in the art. These formulations will typically be oral formulation such as tablets, coated tablets (such as controlled release tablets), capsules, suspensions, solutions, syrups, powders, or emulsions but may be formulations for inhalation (such as powders or aerosols), transdermal absorption (such as patches) or for parenteral (e.g subcutaneous, intramuscular or intravenous) ocular or rectal administration in the form of, for example, sterile saline solutions, drops or suppositories. Where the treatment is to be, for example, to reduce the inflammatory reactions relating to asthma, inhalable preparations will be most suitable and for some allergic conditions such a hay fever, nasal sprays may be most effective. Equally, topical preparations such as drops, creams or gels will be more suitable for ocular conditions or localised skin conditions.

The compounds of formula I and salts thereof may be formulated with conventional pharmaceutical carriers, diluents and/or excipients such as aqueous carriers (e.g. water for injections), binders, fillers, stabilizers, osmolality adjusting agents, effervescing agents, pH buffers and modifiers, viscosity modifiers, sweeteners, lubricants, emulsifiers, flavours, coating agents (e.g. gastric juice resistant coatings) etc.

The dosage of the compounds of formula I or salts thereof administered to a subject will be dependent upon the species, size, maturity, health and condition of the subject, upon the severity of the condition and upon the formulation chosen. Inhalable or intravenous formulations, for example, may deliver a larger proportion of the active agent to the subject than oral formulations and topical treatment will typically require lower doses than systemic treatment. Generally, doses will be in the range of 0.05 to 2000 mg/day, more typically 0.2 to 1000 mg/day, especially 0.5 to 200 mg/day. Administration will typically be once, twice, three or four times per day but may more or less often (e.g. five or six times per day, once every two or three days, or every time symptoms are detected) if appropriate. Topical treatment will typically be administered more often than systemic treatments.

Where the compounds of the present invention are administered as a tonic, such as to reduce lethargy, the symptoms of old age or to boost the immune system, they may be formulated as pharmaceuticals as above. Alternatively, the compounds may be formulated as functional foods or beverages, in which situation the carriers and excipients will typically be edible food or beverage products. Such products may be processed foods for consumption hot, such as ready meals but will more preferably be cold foods including spreads (e.g margarine or low-fat spreads), jams, still or carbonated soft drinks, fruit juice, breakfast cereals, breakfast bars, breads, biscuits, ice-creams, chilled desserts such as yoghurts, mousses or trifles, milk or milk based drinks.

Where the compounds of the invention are formulated as functional foods or beverages, it will be important that the maximum dose which can be accidentally consumed by overeating such foods is not excessive. In such cases, the dosage present in one portion of such functional foods will typically be no more than 5 000 times legs than the lethal dose, more preferably no more than 10 000 times less and most preferably no more than 100 000 times less than the human lethal dose.

Where the compounds of the invention are referred to herein as salts, these will generally be pharmaceutically acceptable salts i.e. those with physiologically tolerable counterions. Such ions include sodium, calcium, organic amines, halides (especially chloride), phosphates, hydrogen carbonates etc.

Without being bound by theory, the effect of the compounds, compositions and medicaments of the invention is believed in part to be the result of a stimulating and modulating effect upon certain aspects of the mammalian immune and defence systems, particularly, for example, by enhancing macrophage activity, acute phase protein (APP) level and white blood cell (WBC) count. The "tonic" effect of the compositions may therefore be, at least partially, attributable to a "cleanup" effect, in which the body is stimulated to remove not only infectious agents but also cell debris and other unwanted matter. In addition, and in spite of their effect as WBC stimulants, the compounds of the invention may show effects as T-lymphocyte and monocyte activation inhibitors and,modulators of interlukins. By such a processes, the tendency for the immune system to generate unwanted inflammation both in general and as a result of encountering biological debris is reduced, as is the danger of autoimmune reaction. As a result, the subject is provided with a better quality of life and the immune system is stimulated and the body purged of some unnecessary and even detrimental antigens. This tonic effect may be applied during or following treatment for a primary disease, condition or infection, or may be an end in itself, when, for example, infection, drug treatment or the aging process has resulted in compromised immune function or a build up of unwanted, immunogenic and/or inflammatory matter in the system.

The stimulation of APP in particular is believe to induce a cleanup of the system, removing cell debris that would otherwise stimulate inflammation and may present native antigens that could induce autoimmune responses. The breakdown products of host cells can also induce the death of neighbouring cells, thereby causing a cascade of cell death and inflammation. Unusually, the compounds of the present invention typically stimulate acute phase proteins without inducing significant fever and are not typically general immune-suppressants.

An alternative method for bringing about a cleanup of biological debris is binding by certain plasma proteins such as particular immunoglobulin Ms (IgMs) with specificity for the membrane phospholipids of dead (but not living) cells, b2 glycoprotein I, clusterin and serum amyloid P. Such mechanisms may also be modulated by the compounds of the present invention.

Diseases of collagen, such as systemic lupus, are for example believed to have a build up of cell debris as a primary cause in many cases. As a result, the compounds of the present invention are highly suitable for the treatment or prevention of collagenous disease, for example in those showing symptoms of the disease or those having a predisposition due to inheritance or injury.

Similarly, a build up of biological debris is a particular problem in Multiple Sclerosis and may only be treated by existing agents having considerable side-effects, such as β-interferon. The compounds of the present invention allow a more targeted stimulation of APP and consequent removal of debris which may be highly valuable in such cases. Cell debris is also believed to contribute to Alzheimer's, Parkinson's and Huntinton's diseases.

The tonic effect of the compounds of the present invention in older subjects may also be explicable as a result of a cleanup mechanism. As subjects age, a greater proportion of cells suffer programmed cell death due to telomere reduction and apoptosis. At the same time, the level of clean up mechanisms such as APPs and the effectiveness of the immune system typically declines. This may lead to a build up of debris and a susceptibility of infection, these factors then leading to degenerative diseases and conditions such as heart attacks. By prophylactic treatment with the compounds of the present invention, the immune system and APP levels may be stimulated reducing the debris buildup and causing the immune system to rid the body of infections before catastrophic events such as bursting of blood vessels causes conditions such as heart attacks.

In a similar way to that seen in aging subjects, those suffering from chronic disease may experience a build up of biological debris from both host cells and infectious agents. The compounds of the present invention may be administered to speed recovery and improve quality of life in such cases. This mechanism is also suitable for speeding the recovery of any subject after events such as malaria, surgery, burns or sepsis.

The immune stimulation and cleanup effect of the compounds of the invention may be used in combination with other drugs, particularly to improve the quality of life of subjects having compromised immune function resulting from a primary condition or the treatment therefore. For example, patients suffering from HIv and related conditions may be treated with one or more antireteroviral agents in order to treat or control the disease. Examples of these include reverse transcriptase inhibitors and protease inhibitors such as zidovudine, didanovine, zalcitabine, stavudine, lamivudine, nevirapine, delavirdine, indinavir, ritonavir, nelfinavir, hydroxyurea kolchicine, AZT and 2',3'-dideoxyinosine (ddI). In combination with this treatment, the compounds, compositions or medicaments of the invention may be administered in order to purge and stimulate the patients remaining immune function.

Similarly, subjects suffering from a hyperplastic or neoplastic disease such as cancer or leukemia may be treated with one or more cytotoxic agents (such as nucleoside analogues), by surgery, external beam irradiation and/or radionuclide therapy. In such cases, the immune system of the subject is generally suppressed as a side effect of the therapy. The immune system may, however, be boosted by administration of the compounds of the present invention in order to provide the subject with lower susceptibility to infection during and after the primary therapy. In addition, the compounds or compositions of the present invention may be administered to stimulate or focus an immune response (particularly, for example by the stimulation of macrophages) against any remaining tumour cells, micro-tumours or micro-metastases in order to provide more complete remission of the disease. Such treatment may be carried out during or after treatment by other agents or interventions.

The compounds of the present invention may also be used to stimulate the destruction (particularly by macrophages) of micro-tumours and thereby prevent the formation or spread of neoplastic disease. This will apply particularly in older subjects (see below) or those considered as having a predisposition to neoplastic disease (e.g. due to heredity; exposure to predisposing chemical or physical environments, such as carcinogens, ionising radiation, etc; previous treatment for neoplastic disease; results of genetic testing etc).

In a further preferred aspect, the present invention therefore provides a method for the treatment of a mammalian (preferably human) subject comprising administration of a compound of formula I or a salt thereof as defined herein, in combination with another drug and/or treatment regime. Preferably, the method is a method for the treatment of a viral, hyperplastic or neoplastic disease, more preferably for the treatment of HIV, cancer or leukaemia. The other drug is preferably an antiviral, such as those listed herein or an antineoplastic agent such as a radiopharmaceutical or chemotherapeutic (e.g. asparaginase, bleomycin, cisplatin, cladribine, cyclophosphomide, cytrabine, dacarbazine, daunorubicin, doxorubicin, etoposide, fluorouracil, hydroxyurea, mercaptopurine, mustine, methotrexate, procarbazine, or vinblastine). The other treatment regime is preferably surgery and/or external beam irradiation. In this method, the compound of the present invention will typically be formulated as a pharmaceutical, either as the sole active agent or in combination with at least one other drug agent and will be administered prior to or preferably consecutively with or after the other drug or treatment.

In a preferred embodiment, the invention also provides a method of prophylaxis against the development of cancer or other neoplastic disease comprising administration of a compound of the invention.

Where symptoms such as fatigue or lethargy are the result of old age or viral, bacterial or fungal infection or the symptoms or treatment of hyperplastic disease such as cancer, the compounds of the present invention may be administered either as a pharmaceutical, or as an additive in, for example a "functional food". Where the cause is a medical condition or treatment, the compound of the invention will generally be taken in the form of a pharmaceutical. Where, however, the cause is simply the result of the general build up of unwanted debris in old age, the compounds of the present invention will preferably be taken in the form of a functional food or dietary supplement for convenience and ease of compliance.

In a preferred aspect, the present invention therefore provides a method of tonic treatment of an aging mammalian (preferably human) subject, or a subject suffering from the aftereffects of infection, disease or treatment, comprising administration of a compound of formula I or a salt thereof as defined herein. Where the subject is an aging human, they will preferably be at least 60 years of age, more preferably at least 70 and most preferably at least 75. The subject may be suffering from an identifiable viral, immune-deficient, autoimmune or allergic disease or condition, or may be a generally healthy subject in these or all respects wishing for a boost in physical or mental energy or in immune functions or a reduction in fatigue or lethargy. The invention also provides for the use of the compounds of the invention in the manufacture of a tonic medicament suitable for use in such methods. Compounds of formula I (and particularly of formulae IIIb or IVb) or salts thereof in which one or preferably both $T_1$ groups are S—$R_6$ (as herein defined) are preferred for this purpose.

In a further aspect of the present invention, the compounds of formula I as described herein may be further substituted at any appropriate position. In particular, a suitable substitution pattern may be chosen so as to control the relative binding of the compounds in which both $T_1$ groups are S—$R_6$ in comparison with the binding of the compound having one $T_1$ group as H and the other as S—R$_6$. It is thought that these two substitution patterns bind differently in vivo and in some circumstances it is preferable to have only the dual-thio-substituted compound bind. In such circumstances, the skilled worker will wish to modify the structures of the compounds described herein, particularly with bulky groups, such that binding of the mono-thiol compound is inhibited but binding of the di-thiol compound is not. Substituent groups such as phenyl groups and tertiary amines are example substituents among many others suitable for this purpose. An appropriate substitution pattern may be established by routine techniques such as multiple-parallel or combinatorial synthesis (such as on a resin support) combined with high-throughput screening against an appropriate biological target such as an isolated enzyme, receptor or appropriate protein fragment.

Where the desired compound of the invention is one of formulae Ib, IIIb or IVb and described herein supra then it may be desirable to inhibit thiol substitution at the positions ortho and/or meta to the R$_1$ group. This could be carried out by any suitable substitution at the ortho and/or meta positions in formula Ib, so as to provide a compound of the invention such as that shown in formula VI;

(VI)

In this aspect, all groups previously described are as defined herein but it is preferable that both T$_1$ groups are S—R$_6$ moieties and particularly glutathione. Each R$_7$ group is independently hydrogen or a substituent preventing thiol subsitiution at the positions ortho or para to R$_1$. Examples include small alkyl or alkenyl groups such as C$_1$ to C$_6$ alkyl or alkenyl (methyl, eithyl, isopropyl etc), hydroxy or alkoxy groups (especially with small alkyl groups as described), halogens (chloro, bromo etc), amines (primary, secondary or tertiary), cyano groups etc. Generally, the position ortho to R$_1$ may be expected to be more accessable for substitution and thus a compound of formula VI wherein both groups R$_7$ meta to R$_1$ are hydrogen is a preferred alternative. Where a hydrogen at position R$_7$ is desired in the final compound of formula I, a blocking group at R$_7$ may be used which can subsequently be removed to leave hydrogen. Suitable examples include amine and nitro groups which may be subsequently removed in known ways such as by dediazoniation. In such a method, the compounds of formula VI (partucularly where both T$_1$ groups are Hydrogen) may be seen as intermediates to certain desired compounds of formula I and especially Ib.

It is further possible that additional thiol substitution may be present in the compounds of the present invention, in addition to the T$_1$ groups as defined herein. In this embodiment, a compound of formula VI is provided wherein R$_7$ is T$_1$ as defined herein and in particular, at least 3 groups of T$_1$ and R$_7$ in formula VI are S—R$_6$ groups.

The present invention will now be illustrated by the following, non-limiting examples and the accompanying drawings, in which.

EXAMPLES

1H-NMR were recorded on a Bruker 300 MHz spectrometer with CDCl$_3$ as solvent. HPLC was performed with a Gynkotek pump equipped with a Symmetry C-18, 5 mm, 3.9×150 mm column and a Gynkotek UVD 170S detector set at 254 nm. Gradient: 1% TFA in water/acetonitrile 70/30 to 0/100 in 8 min.

Example 1

Synthesis of Starting Material-4OH OPB

To a 1-litre round bottom flask with magnetic stirring is charged methanol (450 ml) and oxyphenbutazone hydrate (90.0 g, 0.26 mol). The solution is stirred at ambient temperature and sodium hydroxide solution (2M, 13.5 ml) is added. Hydrogen peroxide (30%, 180 ml) is added drop wise over 10 min. The resulting clear pale yellow solution was stirred for 24 h. The resulting suspension was cooled on an ice bath for 2.5 h and the mixture filtered through a glass filter and sucked dry. The light brown crystals were washed carefully on the filter with MeOH/water (1:2, 200 ml), sucked dry and washed once more with 100 ml of the same solvent mixture. The product was allowed to dry on the filter over night. The crude product was then transferred to a 200 ml round bottom flask, diethyl ether (200 ml) added and the resulting suspension stirred vigorously for approximately 5 min. The mixture was filtered and sucked dry on the filter. The appearance of the product was pale pink after the ether treatment. Crude yield 53 g. The ether treatment procedure was repeated once more with 150 ml of ether. The now almost white material was dissolved in methanol (330 ml) to give a red solution. Water (350 ml) was charged slowly over 35 min to give a white suspension. The solid was collected on a glass filter and dried in vaccuo at 30° C. over night to give 4-OH OPB as a pale pink solid, 31 g, 35%. HPLC>98%. $^1$H NMR confirms identity with reference sample.

Figure 1:
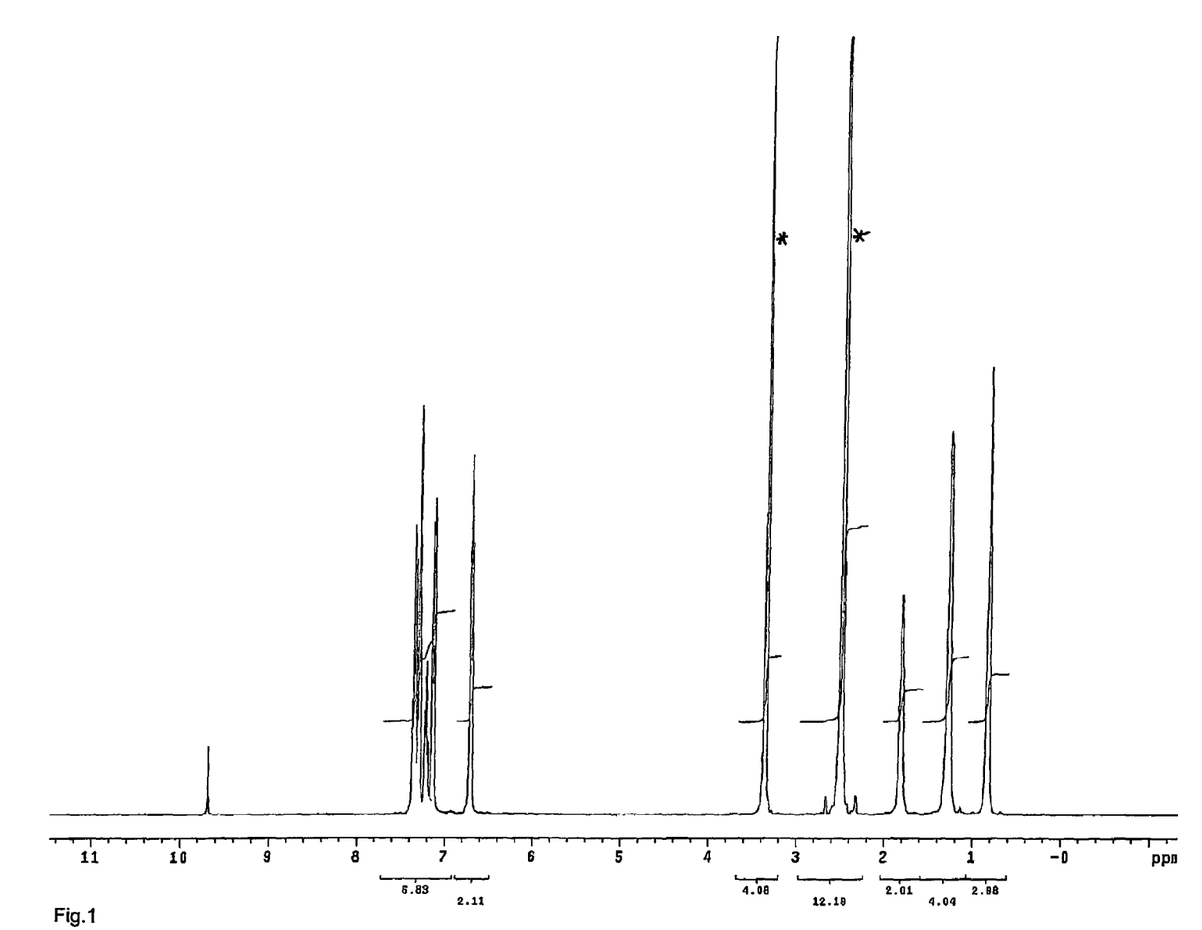
FIG. 1 shows the full NMR spectrum (in dutero DMSO) of 4-OH—OPB.
Figure 2:
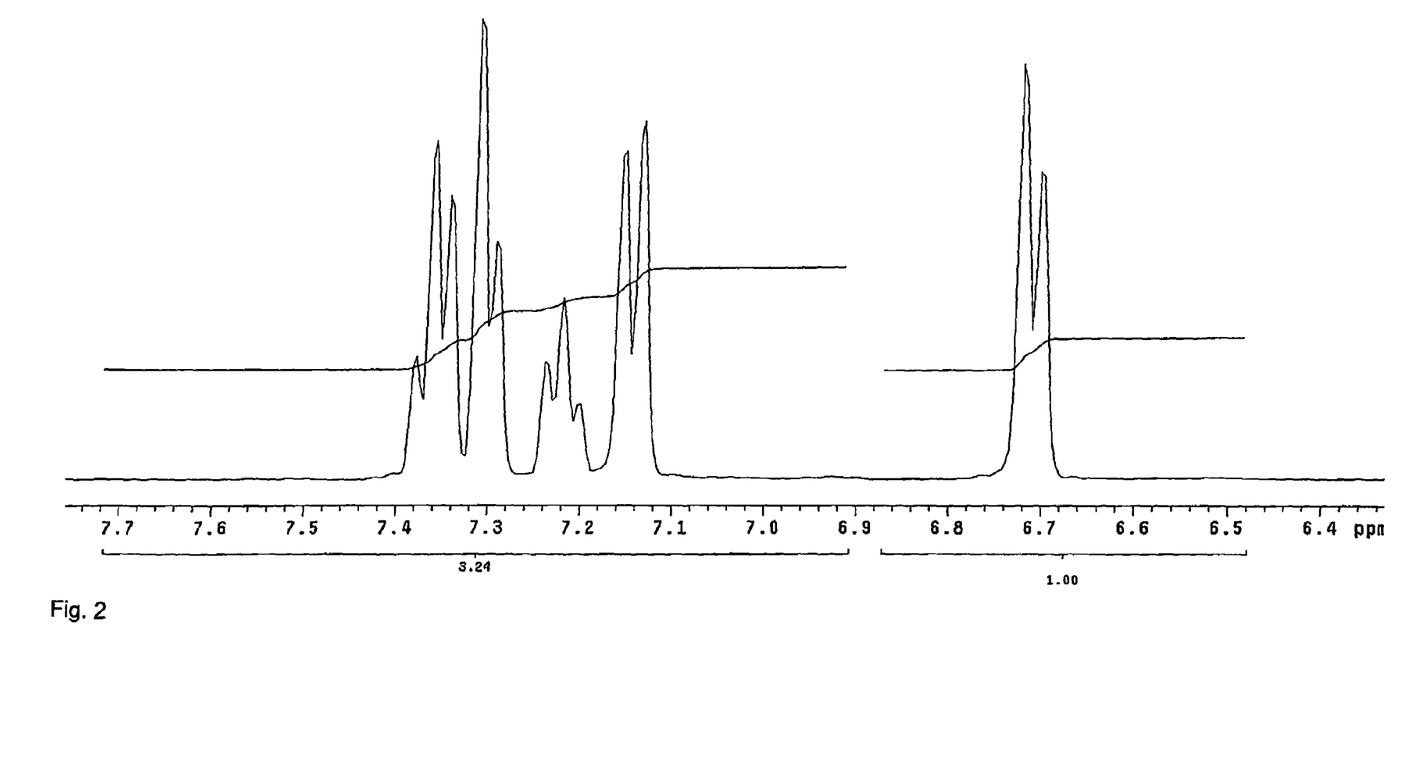
FIG. 2 shows an expansion of the aromatic region of the NMR spectrum (in dutero DMSO) of 4-OH—OPB.

The proton NMR of the starting material is shown in FIGS. 1 (full spectrum) and 2 (aromatic region)

Example 2

Ring Opening

Conversion 4-Hydroxy-oxyphenbutazone (4-OH-OPB) into N-phenyl-2-hydroxy-2 butyl 1,3-propanal quinoneimine (PHBPQ) was carried out by incubation in buffer at pH 7.4, followed by purification by High Performance Liquid Chromatography (HPLC).

Incubation

4-OH-OPB (34 mg) was first dissolved in DMSO (1 ml) before incubation for 15 minutes at 37° C. in PBS to a concentration of 100 μM (100 ml, PBS constituted as below).

Purification

An analytical HPLC run (C18 reversed phase column) was performed to validate the products formed (determination by Mass Spectrometry). The PHPBQ was then purified by loading all 100 mL of the incubation mixture on a preparative column (C18, reversed phase column).

Figure 3:
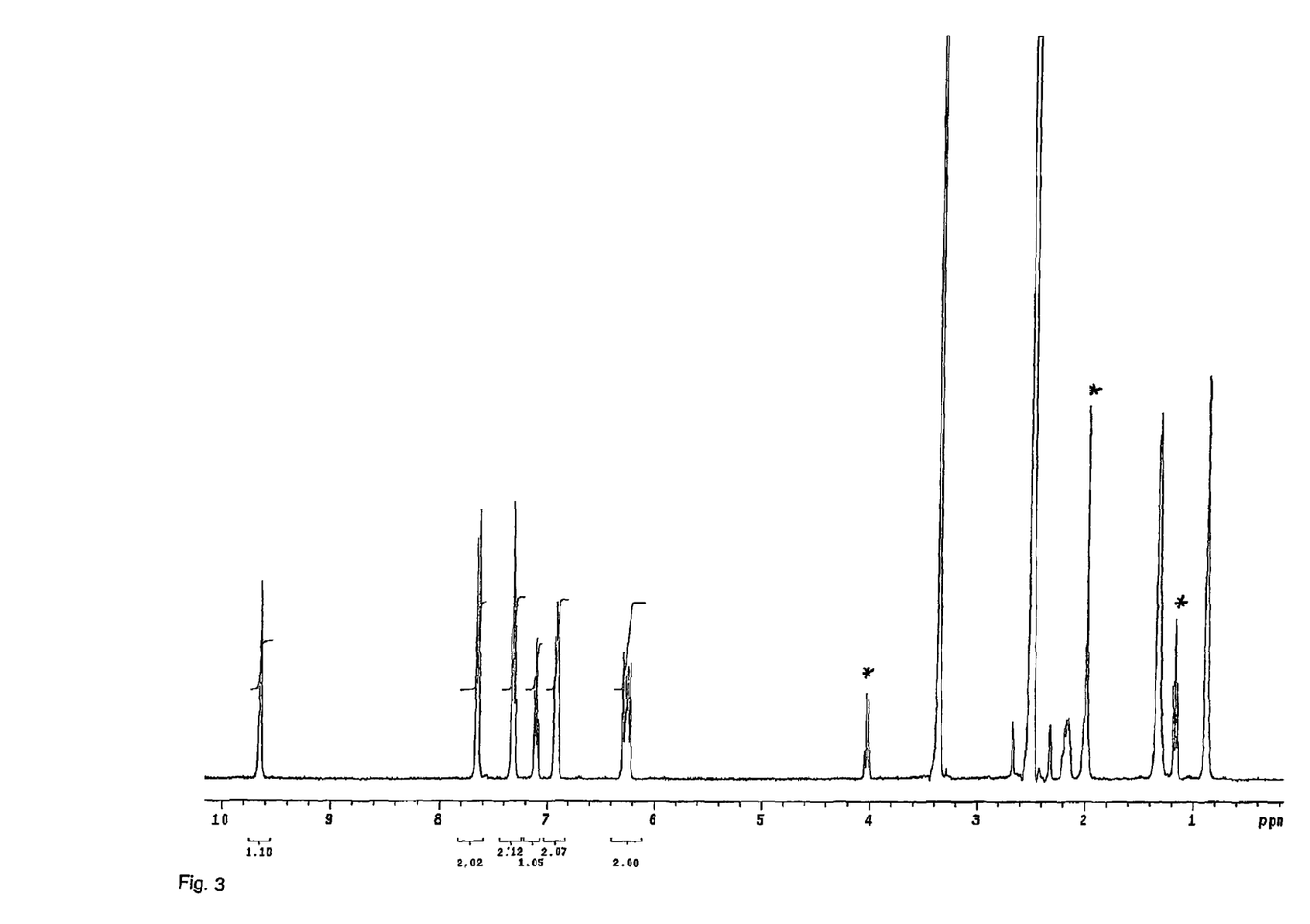
FIG. 3 shows the full NMR spectrum (in dutero DMSO) of PHBPQ.
Figure 4:
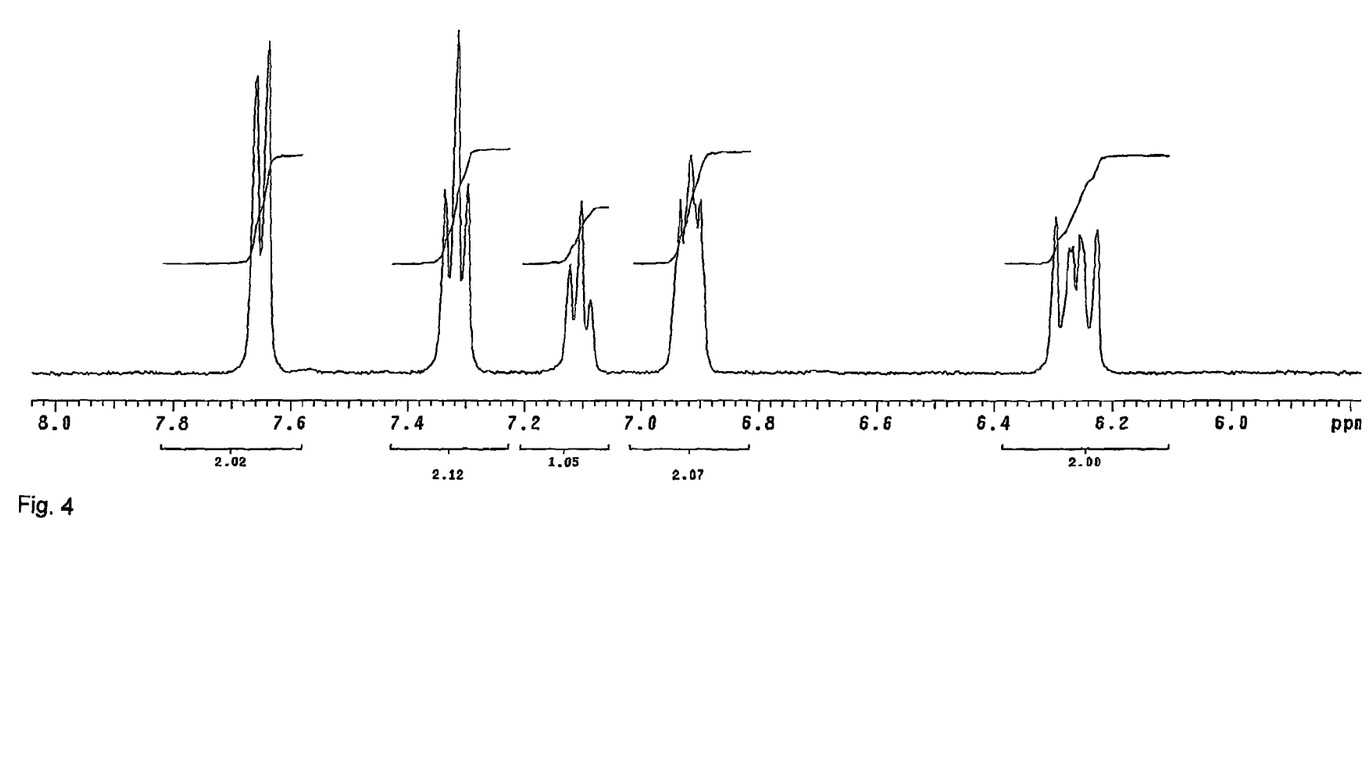
FIG. 4 shows an expansion of the aromatic region of the NMR spectrum (in dutero DMSO) of PHBPQ.

Both analytical and preoperative runs were eluted with gradient eluents, running from 0 acetonitrile to 67% acetonitrile (in deionised water) in the presence of 0.1% TFA to keep the pH at 2. During the preperative run, fractions were collected (peaks) and checked for the right product by Mass Spectrometry. Finally, the identified products are dried under vacuum leaving products with 99% purity. The $^1$H NMR spectrum of the resulting compound is shown in FIG. 3 (full spectrum) and FIG. 4 (aromatic region).

PBS=(phosphate buffered saline, pH 7.4)

NaCl, 8.2 g; Na$_2$HPO$_4$.2H$_2$O, 1.9 g; NaH$_2$PO$_4$.H$_2$O, 0.3 g; Na$^+$, 163, 9 mM; Cl$^-$, 140, 3 mM; HPO$_4^{2-}$, 10, 9 mM; H$_2$PO$_4^-$, 1, 8 mM, Braun Melsungen AG.

Example 3

Analysis of Ring-Opened Product

The product of Example 2 (PHBPQ, N-phenyl-2-hydroxy-2 butyl 1,3-propanal quinoneimine) was examined for stability in aqueous solution, followed by analysis by $^1$H NMR spectroscopy.

The results indicated that PHBPQ was more stable at pH 7.4 than 4-OH-OPB with a half-life of ~2-2.5 hours. The PHBPQ was not re-converted into 4-OH-OPB when the solution was acidified.

Example 4

Thiol Derivitisation

To PHBPQ (prepared as described above in Example 2 (500 μM) but remaining in PBS solution) 1.5 mM glutathione was added and incubated for 30 minutes at 37° C. The mixture was purified by the method described above in Example 2. Approximately equal quantities of product derivatised with one glutathione (PHBPQ-1GSH) and two glutathione (PHBPQ-2GSH) were separated from the mixture.

The Experiment was repeated with the alpha amino acid cysteine as thiol compound. The derivatised products with one cysteine and two cysteines attached were generated.

Figure 5:
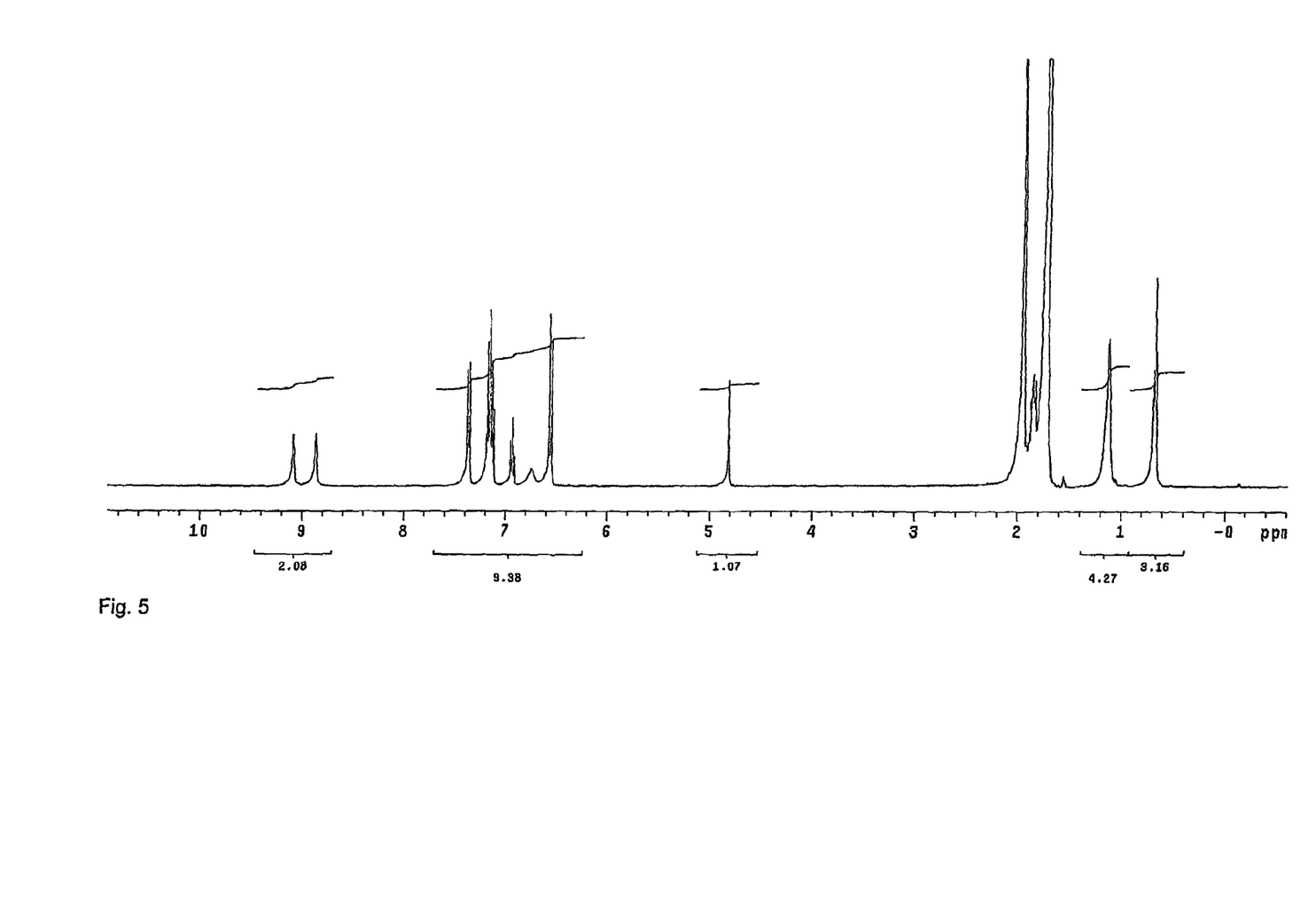
FIG. 5 shows the full NMR spectrum (in dutero DMSO) of PHPBHM.
Figure 6:
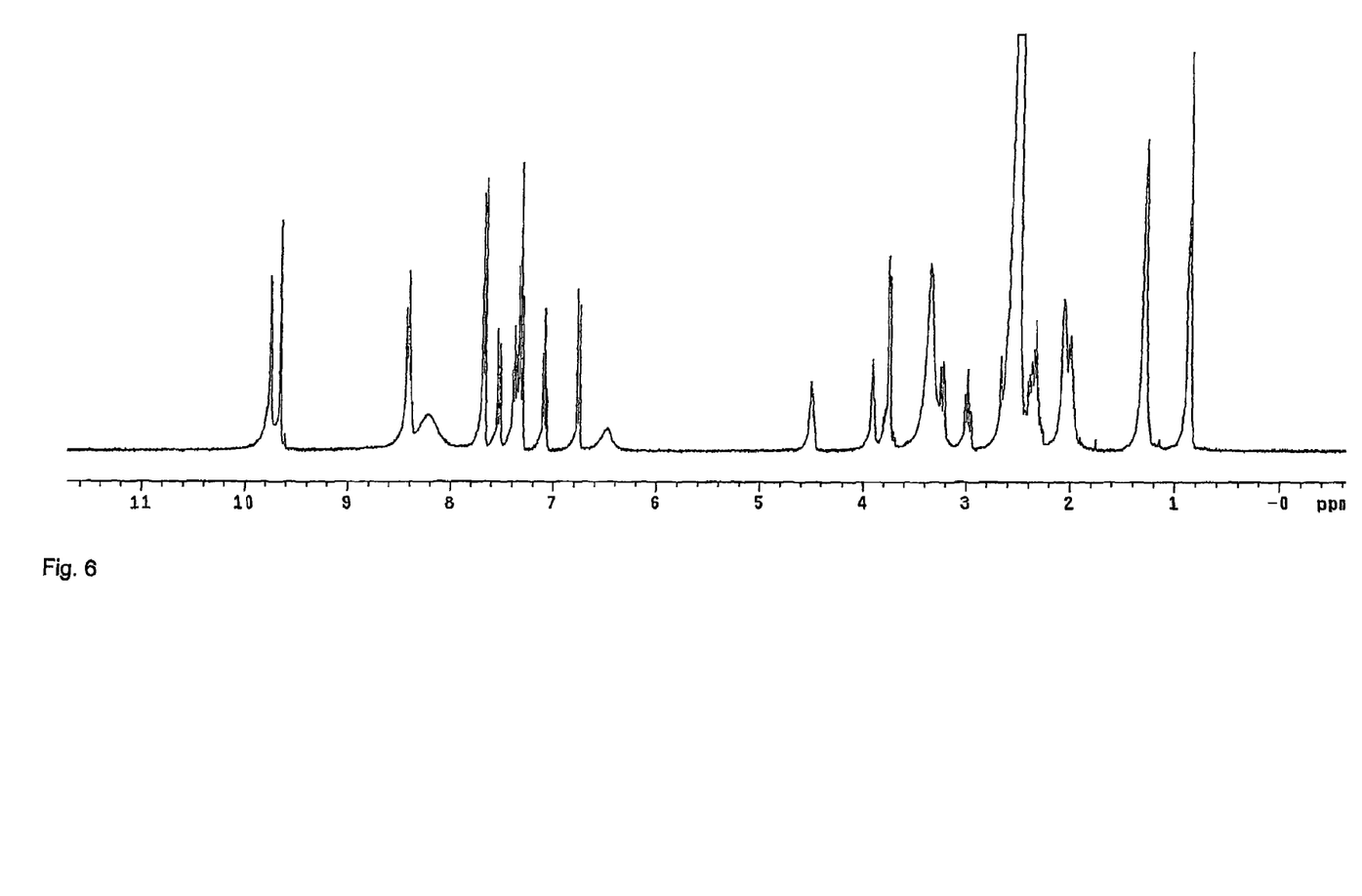
FIG. 6 shows the full NMR spectrum (in dutero DMSO) of PHBPQ-1GSH.
Figure 7:
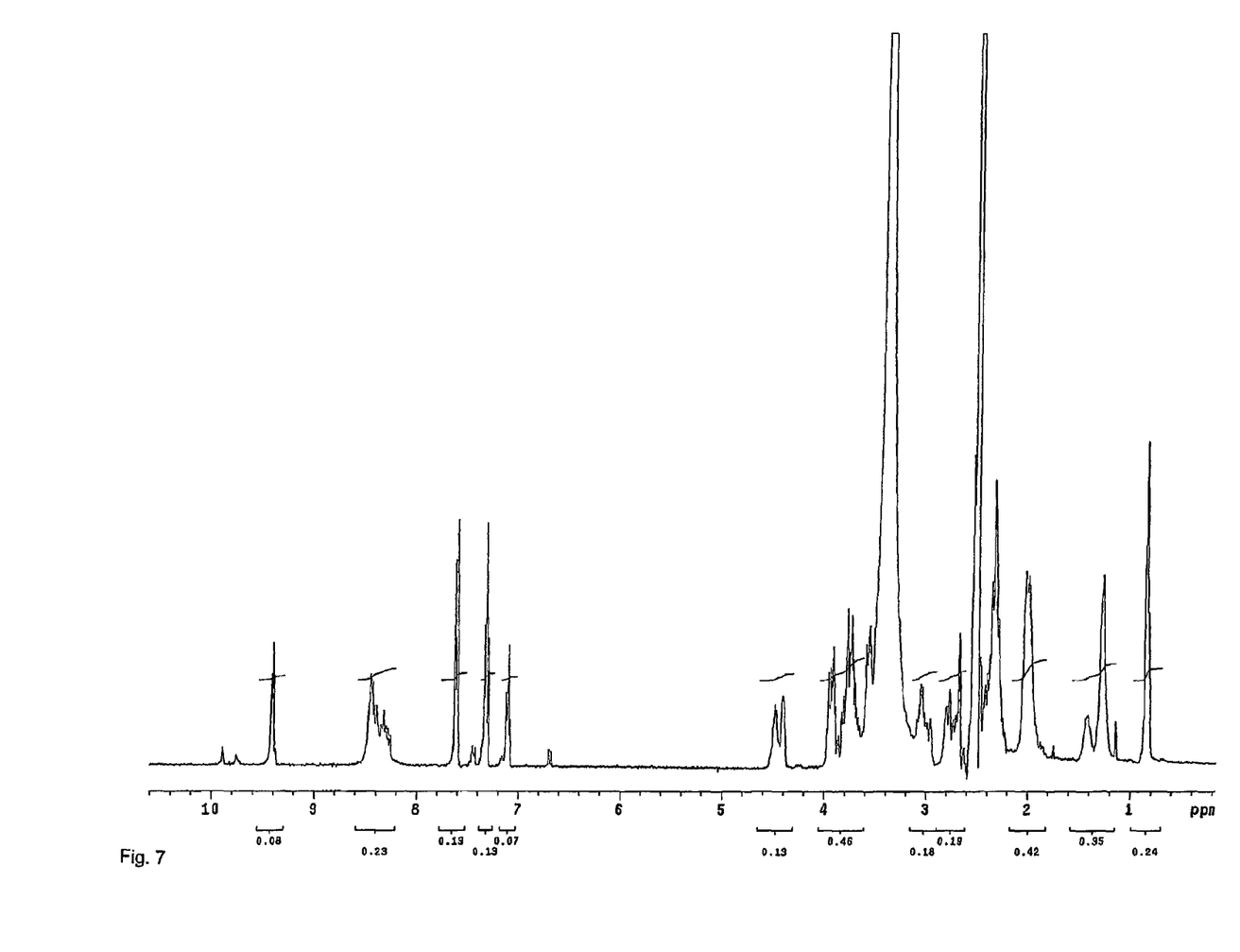
FIG. 7 shows the full NMR spectrum (in dutero DMSO) of PHBPQ-2GSH.

Also generated in these experiments was a further comopund of the present invention, in which the GSH groups are eliminated and the ring aromatised to form N-phenyl, N'-parahydroxyphenyl, 2-butyl, 2-hydroxy malonamide (PHPBHM). The proton NMR spectrum of this compound are shown in FIG. 5. The specta of PHBPQ-1GSN and PHBPQ-2GSH are shown in FIGS. 6 and 7 respectively.

Example 5

Suppression of Cytokine Production

Figure 8:
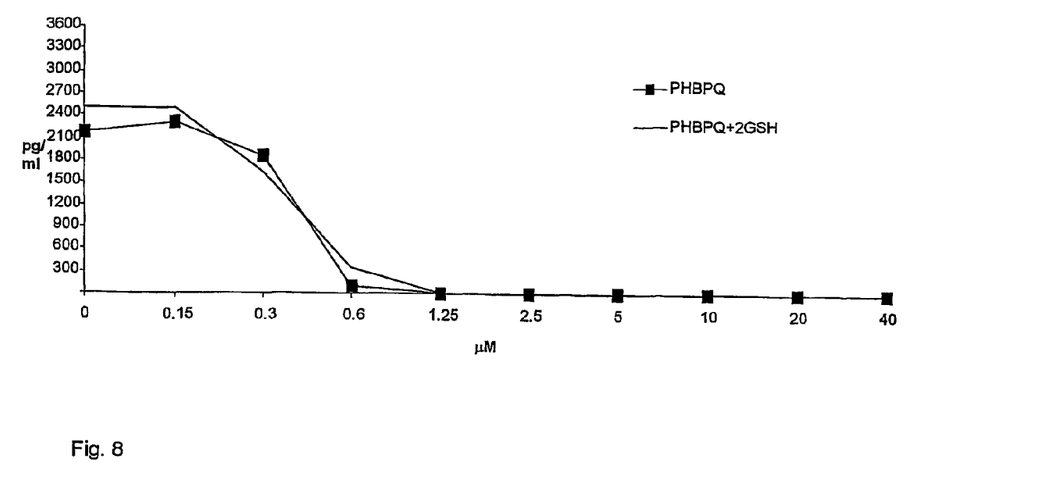
FIG. 8 shows the effect on Interleukin 6 (IL-6) production of mononuclear cells (MNC) after incubation with PHBPQ and PHBPQ-2GSH.
Figure 9:
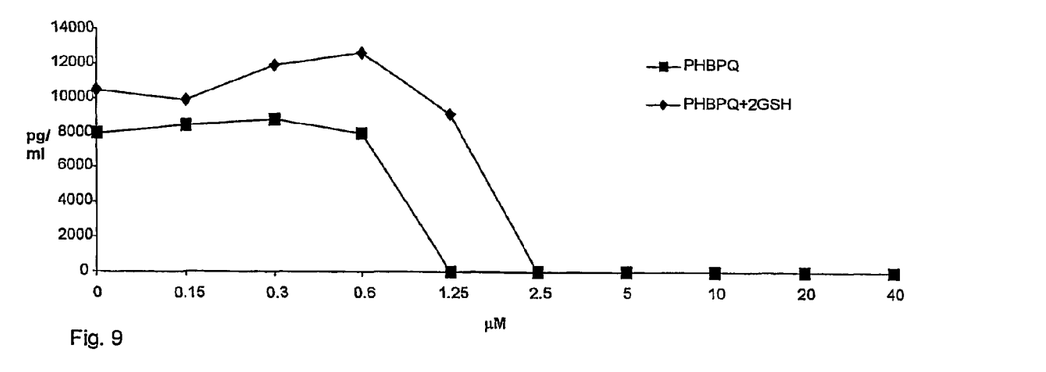
FIG. 9 shows,the effect on Granulocyte Colony-Stimulating Factor (GM-CSF) production of mononuclear cells (MNC) after incubation with PHBPQ and PHBPQ-2GSH.

The PHBPQ, as prepared in Example 2 and the PHBPQ-2GSH as prepared in Example 4 were incubated with isolated human mononuclear cells (MNC) derived from peripheral blood from healthy volunteers. Production of the cytokines Interleukin-6 (IL6) and Granulocyte Colony-Stimulating Factor (GM-CSF) was measured. The results (shown in FIGS. 8 and 9) indicates that 0.5-2 μM PHBQ or PHBQ-2GSH is sufficient to completely block production of the measured cytokines.

The invention claimed is:

1. An optionally substituted compound of formula III:

(III)

wherein each $T_1$ is independently, absent, hydrogen or an S-R$_6$ group, where any/each R$_6$ is independently an organic group of molecular weight up to around 500 amu, R$_2$ is an optionally substituted alkyl, alkenyl, alkynyl, alkaryl, aralkyl, arylsulphonylalkyl or aralkenyl group, and R$_3$ is hydrogen or a C$_2$-C$_7$, acyl, or alkaryl group and R$_5$ is hydrogen or an alkyl, alkenyl group, OH, O-alkyl, O-acyl, SH, S-alkyl, S-acyl, halo, or amino group.

2. A compound as claimed in claim 1 of formula IV, or a salt thereof;

(IV)

wherein R$_5$ is hydrogen or OH and each $T_1$ is, independently, H or a glutathione moiety attached via the sulphur atom thereof.

3. A compound as claimed in claim 1 wherein both $T_1$ groups are independently thiols, attached by the sulphur atom thereof.

4. A compound as claimed in claim 3 wherein both of said thiols are independently glutathione or cysteine.

5. A compound as claimed in claim 1 wherein both $T_1$ groups are hydrogen.

6. A compound of claim 1 wherein the two $T_1$ groups are independently ortho or meta to group R$_1$.

7. A compound as claimed in claim 1 wherein one $T_1$ group is ipso to group R$_1$ and one $T_1$ group is para to group R$_1$.

8. A compound as claimed in claim 1 having a formula IIIa, IIIb, IVa and/or IVb (IIIa)

-continued wherein R$_1$-R$_5$, T$_1$ and X are as defined in claim 1.

9. A method for the synthesis of a compound as defined in claim 1 by ring-opening of a starting material of formula II wherein T$_1$, R$_1$, R$_2$, R$_3$, R$_4$, and X are as defined in claim 1, or protected derivatives or precursors thereof.

10. A method of claim 9 wherein the two T$_1$ groups are independently ortho or beta to group R$_1$.

11. A method as claimed in claim 9 wherein a compound of formula II having hydrogens at both T$_1$ positions is subjected to ring-opening followed by reaction with a thiol to provide a compound as claimed in claim 1 wherein at least one T$_1$, group is a thiol.

12. A pharmaceutical composition comprising a compound as claimed in claim 1 and at least one pharmaceutically acceptable excipient, carrier or diluent.

\* \* \* \* \*

UNITED STATES PATENT AND TRADEMARK OFFICE
CERTIFICATE OF CORRECTION

PATENT NO. : 7,663,000 B2
APPLICATION NO. : 10/565506
DATED : February 16, 2010
INVENTOR(S) : Dekkers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 715 days.

Signed and Sealed this

Fourth Day of January, 2011

David J. Kappos
*Director of the United States Patent and Trademark Office*